US008143409B2

(12) United States Patent
Barreca et al.

(10) Patent No.: US 8,143,409 B2
(45) Date of Patent: Mar. 27, 2012

(54) CRYSTALLINE FORM OF RABEPRAZOLE SODIUM

(75) Inventors: Giuseppe Barreca, Montevecchia (IT); Alessandro Restelli, Bareggio (IT); Pietro Allegrini, San Donato Milanese (IT)

(73) Assignee: Dipharma Francis S.R.L., Baranzate (IT)

( * ) Notice: Subject to any disclaimer, the term of this patent is extended or adjusted under 35 U.S.C. 154(b) by 1050 days.

(21) Appl. No.: 11/958,881

(22) Filed: Dec. 18, 2007

(65) Prior Publication Data

US 2008/0161359 A1 Jul. 3, 2008

(30) Foreign Application Priority Data

Dec. 19, 2006 (IT) .............................. MI2006A2449

(51) Int. Cl.
*C07D 401/12* (2006.01)
(52) U.S. Cl. .................................................... 546/273.7
(58) Field of Classification Search ............... 546/273.7; 514/338
See application file for complete search history.

(56) References Cited

U.S. PATENT DOCUMENTS

| 3,944,522 | A | 3/1976 | Tohyama et al. | |
|---|---|---|---|---|
| 4,072,699 | A | 2/1978 | Merkl | |
| 5,023,269 | A | 6/1991 | Robertson et al. | |
| 5,045,552 | A * | 9/1991 | Souda et al. | 514/338 |
| 6,379,650 | B1 | 4/2002 | Ashton | |
| 6,627,646 | B2 * | 9/2003 | Bakale et al. | 514/322 |
| 7,183,272 | B2 | 2/2007 | Aronhime et al. | |
| 7,629,372 | B2 | 12/2009 | Dropinski et al. | |
| 7,879,867 | B2 | 2/2011 | Paredes et al. | |
| 7,897,613 | B2 | 3/2011 | Arul et al. | |
| 2004/0180935 | A1 | 9/2004 | Venkatraman et al. | |
| 2006/0135565 | A1 * | 6/2006 | Malpezzi et al. | 514/338 |
| 2006/0288373 | A1 * | 12/2006 | Grimes et al. | 725/62 |

FOREIGN PATENT DOCUMENTS

| EP | 0268956 B2 | 4/1988 |
|---|---|---|
| EP | 1674463 A1 | 6/2006 |
| EP | 1 693 361 A1 | 8/2006 |
| JP | 2001-039975 A | 2/2001 |
| WO | 03/082858 A1 | 10/2003 |
| WO | 03101452 A1 | 12/2003 |
| WO | 2004063188 A1 | 7/2004 |
| WO | 2004100500 A2 | 11/2004 |

OTHER PUBLICATIONS

Vippagunta et al., "Crystalline solids", Advanced Drug Delivery Reviews 48 (2001) 3-26.*
Silverman, The Organic Chemistry of Drug Design and Drug Action, NY: Academic Press, Inc. 1993, 72-76.*
Rowland and Tozer. "Clinical Pharmacokinetics, etc.," 1995, p. 123.*
Wilbraham et al. "Organic and biochemistry . . . " p. 250-251 (1985).*
Garattini "Active drug metabolites . . . " Clin. Pharmacokinetics v.10, p. 216-227 (1985).*
CMU Pharmaceutical polymorphism, intenet p. 1-3 (2002) (printout Apr. 3, 2008).*
Singhal et al., "Drug polymorphism, etc., "Advanced drug delivery reviews 56, 335-347 (2004).*
Concise Encyclopedia, NY: Walter de Gruyter Berlin, 1994, 872-875.*
European Search Report issued in the corresponding European Application No. 07009205.1 Completed on Mar. 28, 2008 and Mailed on Mar. 28, 2008.
New Drug Application (NDA) No. 020973, Annotated Package Insert, Mar. 5, 1999, pp. 1-17.
E Doelker, "Physicochemical Behaviors of Active Substances Their Consequences . . . ", S.T.P. Pharma Pratiques (1999) 9, (5) 399-409, pp. 1-33.
J. Bernstein, Polymorphism in Molecular Crystals, Oxford: Clarendon Press, 2002, pp. 117, 118, 272 and 273.
M. Davidovich et al., "Detection of Polymorphism by Powder X-Ray Diffraction: Interference . . . " American Pharmaceutical Review, Indianapolis, Indiana, Russell Pub., 2004 7(1), pp. 10, 12, 14, 16 and 100.
M. R Caira, Crystalline Polymorphism of Organic Compounds, "Topics in Current Chemistry," vol. 198, Springer Verlag Berlin Heidelberg 1998, pp. 163-208.
J. Halebian et al., "Pharmaceutical Applications of Polymorphism," Journal of Pharmaceutical Sciences, vol. 58, No. 8, Aug. 1969, pp. 911-929.
Chemical & Engineering News, Feb. 24, 2003, pp. 32-35.
H.G. Brittain, "Polymorphism in Pharmaceutical Solids," Marcel Dekker, Inc. 1999, pp. 1-2, 125-181, 183-226.
U.S. Pharmacopia #23, National Formulary #18, 1995, pp. 1843-1844.
N.A. Muzaffar et al., "Polymorphism and Drug Availability," Journal of Pharmacy (Lahore) (1979), 1 (1), pp. 59-66.
N.K. Jain et al., Polymorphism in Pharmacy, Indian Drugs, 1986, 23 (6), pp. 315-329.
E. Doelker, 132:325872 and S.T.P. Pharma Pratiques (1999), 9 (5), 399-409.
P.F. Taday et al., "Using Terahertz Pulse Spectroscopy to Study the Crystalline Structure of a Drug: A Case . . . ", Journal of Pharmaceutical Sciences, vol. 92, No. 4, Apr. 2003, pp. 831-838.
M. Otsuka et al., "Effect of Polymorphic Forms of Bulk Powders on Pharmaceutical Properties of Carbamazepine Granules," Chem. Pharm, Bull, vol. 47 (6), pp. 852-856 (1999).
L. Ulicky et al., "Comprehensive Dictionary of Physical Chemistry," NY, PTR Prentice Hall, 1992, p. 21.
US. Office Action issued in co-pending U.S. Appl. No. 11/311,141, dated Jul. 6, 2007.

(Continued)

*Primary Examiner* — Patricia Morris
(74) *Attorney, Agent, or Firm* — Griffin & Szipl, P.C.

(57) ABSTRACT

Rabeprazole sodium in the monohydrate crystalline form, pharmaceutical compositions thereof, the use thereof in therapy, a process for its preparation, and the use thereof for the purification of rabeprazole sodium.

5 Claims, 2 Drawing Sheets

OTHER PUBLICATIONS

Figure 1:
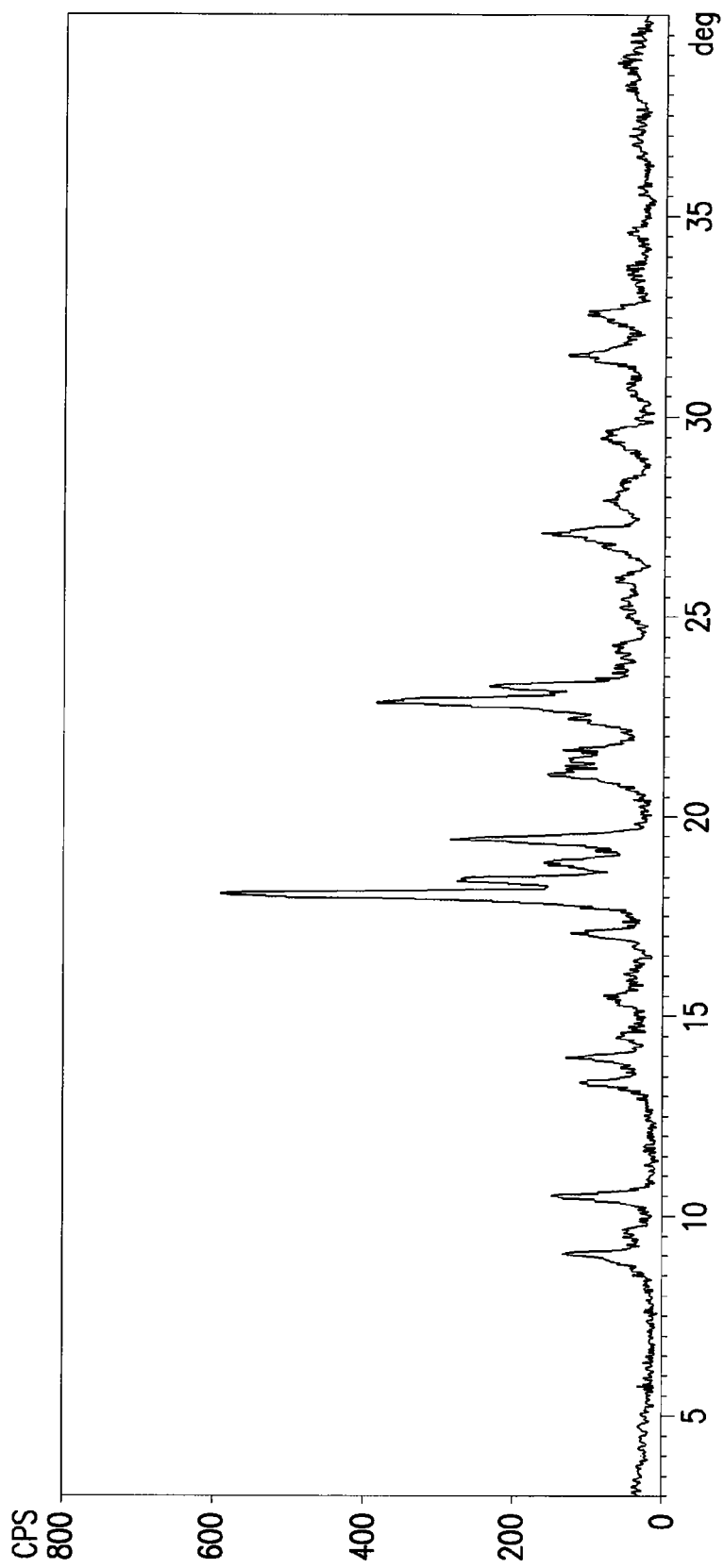

US. Office Action issued in co-pending U.S. Appl. No. 11/311,141, dated Dec. 19, 2006.

M. Eagleson, Concise Encyclopedia Chemistry, New York, 1994, pp. 872-873.

* cited by examiner

CRYSTALLINE FORM OF RABEPRAZOLE SODIUM

This application claims priority from Italian Patent Application No. MI2006A002449, filed Dec. 19, 2006, the entire disclosure of which is incorporated herein by reference.

FIELD OF THE INVENTION

The present invention relates to a novel monohydrate crystalline form of rabeprazole sodium, a pharmaceutical composition thereof, its use in therapy, a process for its preparation and its use in a process for the purification of rabeprazole sodium.

TECHNOLOGICAL BACKGROUND

Rabeprazole sodium, namely 2-[[[4-(3-methoxypropoxy)-3-methyl-2-pyridinyl]-methyl]sulfinyl]-1H-benzylimidazole sodium salt, of formula

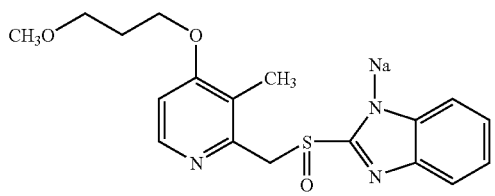

is a gastric secretion inhibitor used for the treatment of peptic ulcer.

EP 268956 discloses the preparation of rabeprazole sodium by crystallization from ethyl ether, to obtain white crystals, having m.p. 140-141° C. (dec.). To date, six crystalline forms of rabeprazole sodium have been described, namely the one referred to as form II in JP 2001-39975, which is obtained starting from solid, non-crystalloid rabeprazole sodium; those referred to as forms X and Y in WO 03/082858; and that referred to as form Z in US patent application 2004/0180935. WO 03/082858 also mentions and claims the hydrated forms of the X and Y forms, but it neither discloses nor characterizes the preparation thereof. Finally, EP 1674463 discloses rabeprazole sodium in the crystalline hydrate form, in particular the two isomorphic forms alpha (substantially hemihydrate) and beta (substantially sesquihydrate). Different forms of biologically active compounds, in particular the polymorphic forms, are known to be useful both in therapy, thanks to their different bioavailabilities, release times and solubilities, and in the pharmaceutical technique for the preparation of formulations, as the physical characteristics often accompanying the different physical forms of the drug, such as hygroscopicity, flowability and/or powder compaction, can be advantageously exploited. In particular, the isomorphic forms alpha and beta are characterized by low hygroscopicity, which makes handling and storing easy.

The preparation of these crystalline forms is however rather difficult from the industrial point of view, in that they tend to transform into other crystalline forms or mixtures thereof.

There is therefore the need for a more stable crystalline hydrate form.

SUMMARY OF THE INVENTION

It has now been found that rabeprazole sodium hydrate can exist, in addition to said hydrated crystalline forms alpha and beta, also in a crystalline hydrate form, herein referred to as Form γ, which is more stable at room temperature.

The invention therefore provides rabeprazole sodium in the crystalline hydrate form as Form γ, a process for its preparation, a pharmaceutical composition containing said form and its use in therapy.

A further object of the invention is a process for the purification of rabeprazole sodium by use of said crystalline hydrate Form γ to obtain rabeprazole sodium of suitable quality to fulfill the regulatory requirements for therapeutical products.

BRIEF DISCLOSURE OF THE FIGURE AND ANALYTIC METHODS

The crystalline hydrate Form γ of rabeprazole sodium of the invention was characterized by X-ray powder diffraction (XRPD), by 1H-NMR nuclear magnetic resonance spectrometry and by differential scanning calorimetry (DSC). The water content in the compound was determined by titration with Karl-Fischer technique.

The X-ray diffraction spectrum (XRPD) was recorded with an APD 2000 θ/θ automatic diffractometer for powders and liquids (Ital-Structures), under the following operative conditions: CuKα radiation ($\lambda$=1.5418 Å), scanning with angular interval 3-40° in 2θ, with angular step of 0.03° for a time of 1 sec. The 1H-NMR spectrum was recorded with a Varian Mercury 300 spectrometer, using DMSO-d6 as the solvent.

DSC thermograms were recorded with a Mettler-Toledo differential scansion calorimeter DSC 822, under the following operative conditions: aluminium capsules, 30-400° C. range with increase of 10° C./min, under nitrogen as purging gas (80 ml/min).

Figure 2:
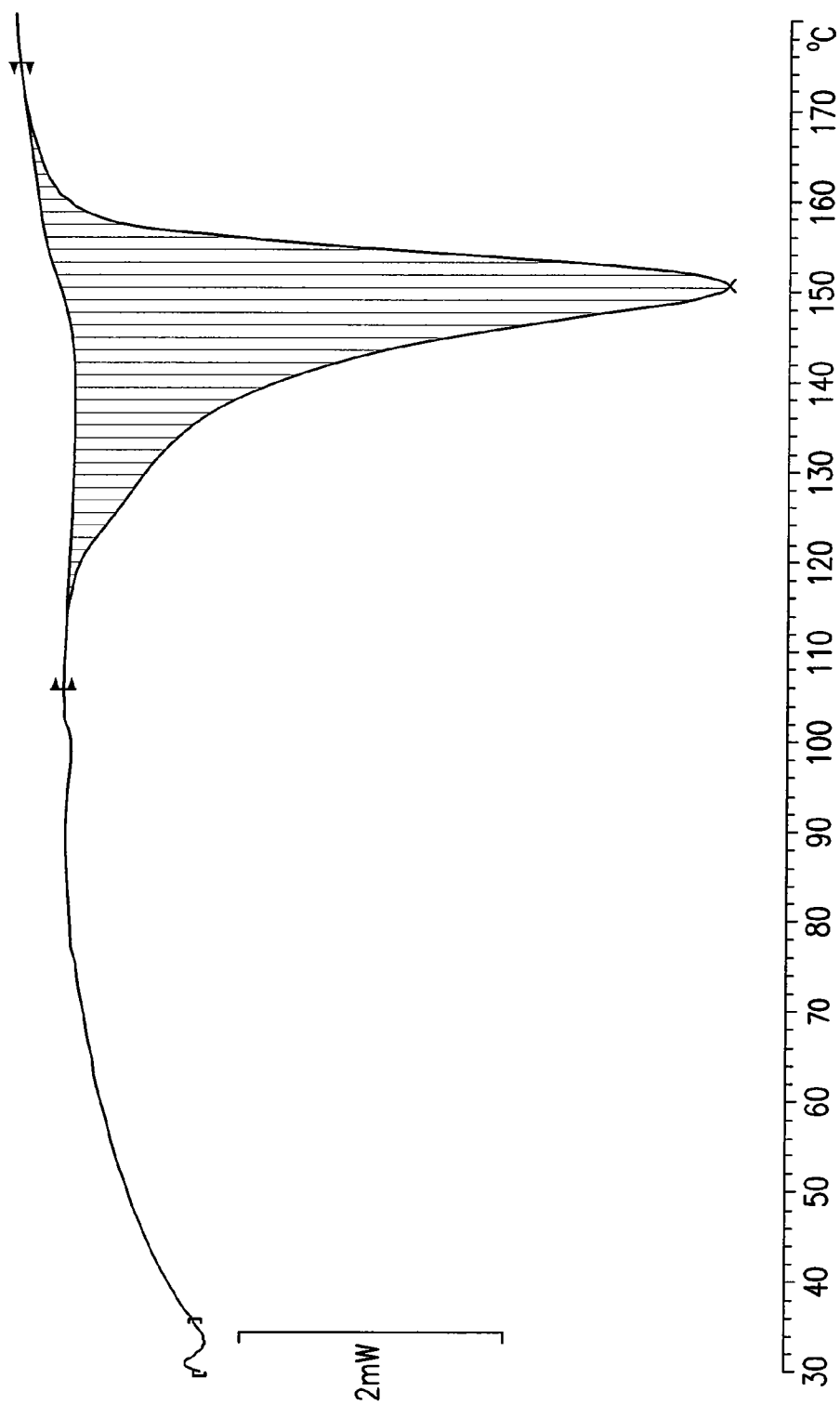

FIG. 1: XRPD spectrum of rabeprazole sodium Form γ.
FIG. 2: DSC thermogram of rabeprazole sodium Form γ.

DETAILED DISCLOSURE OF THE INVENTION

A first object of the present invention is rabeprazole sodium in the crystalline hydrate form γ. Said hydrate form has water content approximately ranging from 4.5 to 5.0%, preferably approximately from 4.6 to 4.8%, so that it can be defined a substantially monohydrate form. Said substantially monohydrate form, herein referred to as Form γ, has a DSC thermogram substantially as reported in FIG. 2, wherein the endothermic peak is at about 152° C., and an XRPD spectrum substantially as shown in FIG. 1, wherein the most intense diffraction peaks fall at 10.5; 18.0; 18.4; 19.4; 21.1; 21.7; 22.9; 23.3; 27.1; 31.6±0.2° in 2θ.

Rabeprazole sodium in the crystalline hydrate Form γ can be prepared by means of a process comprising:
  dispersing rabeprazole sodium in an organic polar aprotic solvent, and dissolving it to provide a solution thereof;
  optionally seeding with the crystalline Form γ;
  maintaining the solution at room temperature for a time equal to or higher than 24 hours; and
  recovering the resulting solid.

The preparation can be carried out starting from a rabeprazole sodium dispersion in a polar aprotic solvent. The starting crude rabeprazole sodium, can for example be obtained as disclosed in EP 268956. Examples of aprotic polar solvents are lower carboxylic acid alkyl esters or mixtures thereof, typically of formula RCOOR', wherein R is hydrogen or $C_1$-$C_4$ alkyl and R' is $C_1$-$C_4$ alkyl. An alkyl group can be straight or branched. Preferred examples of solvents are ethyl acetate, butyl acetate, isopropyl acetate, ethyl propionate, isobutyl propionate and ethyl butyrate or mixtures of two or three of them. More preferred are ethyl acetate, isopropyl acetate and butyl acetate, or mixtures of two of them; particularly ethyl acetate. The concentration of rabeprazole sodium in the starting solution can approximately range from 2 to 30% w/w, preferably approximately from 15 to 20% w/w. The temperature of the dispersion is then raised to above 20° C., preferably to approximately 35-45° C., to promote dissolution of rabeprazole sodium. The resulting solution is left to stand at room temperature for a time equal to or higher than 24 hours, preferably approximately ranging from 24 to 40 hours, thereby separating rabeprazole sodium salt in the crystalline hydrate form. If desired, the solution can be seeded with a small amount of crystalline Form γ to promote crystallization.

The crystalline Form γ can be recovered with known techniques, such as filtration or centrifugation, preferably by filtration, followed by drying under vacuum. The product is dried at a temperature depending on the solvent used. The term "approximately" as used in the disclosure of the invention, means approximately more or less than 10%.

The novel crystalline Form γ of rabeprazole sodium is thermodynamically more stable than the known hydrate forms α and β, as it can be appreciated by comparing the respective DSC thermograms.

Rabeprazole sodium crystalline hydrate, in particular as the Form γ, analogously to commercially available rabeprazole sodium, is useful as a gastric secretion inhibitor and can therefore be used e.g. for the treatment of peptic ulcer.

Object of the invention is also a pharmaceutical composition comprising a diluent and/or carrier and, as the active ingredient, rabeprazole sodium salt in the crystalline hydrate form, in particular as Form γ. Said composition, if desired, can further contain at least one of the known rabeprazole forms as the active ingredient.

Known rabeprazole forms are, for example, the rabeprazole sodium salt form described in U.S New Drug Application (NDA) No. 020973 and those disclosed in JP 2001-39975, WO 03/082858, US 2004/0180935 and EP 1674463.

The ratio of rabeprazole sodium salt crystalline hydrate Form γ, to rabeprazole in one or more of the known forms is selected depending on the physical and biological properties thereof and will be decided by the skilled physician.

The pharmaceutical compositions of the invention can be formulated in a variety of pharmaceutical forms for the administration to humans or animals, according to known techniques. Examples of formulations are for example suspensions, emulsions, solutions, capsules, tablets, sugar-coated pills or other known forms. In case of tablets, preferably protracted-release, enteric-coated tablets, the amount of the active ingredient in a single tablet can approximately range from 10 mg to 30 mg, preferably 20 mg. The process of the invention allows to purify the final product from any impurities formed during the process for the synthesis of rabeprazole, deriving from both parasitic reactions and degradation of the product itself. Therefore, a further object of the present invention is a process for the purification of rabeprazole sodium salt, comprising the conversion of crude rabeprazole sodium salt, as obtainable for example according to EP 268956, to rabeprazole sodium salt crystalline Form γ, and, if desired, the subsequent conversion of the resulting novel form to a known rabeprazole form. Said process provides rabeprazole sodium salt, in particular as the crystalline hydrate form, preferably as Form γ, in a purity degree equal to or higher than 99.9%, i.e. of suitable quality to fulfill the regulatory requirements for the therapeutical products.

The following examples illustrate the invention.

EXAMPLE 1

Preparation of Rabeprazole Form γ

100 g of rabeprazole sodium salt (amorphous) is dissolved at approximately 25° C. in 450 ml of ethyl acetate. The solution is kept at approximately 25° C. and 8 ml of sodium bicarbonate saturated solution is added. The mixture is seeded with a small amount of Form γ, then kept under stirring at approximately 25° C. for 25 hours. The resulting white solid is filtered by suction, washed with 100 ml of ethyl acetate and dried under vacuum at 45° C. The resulting product has an XRPD spectrum substantially as reported in FIG. 1 and a DSC thermogram substantially as shown in FIG. 2, which prove that the compound is crystalline. The compound water content determined according to Karl Fischer is approximately 4.5-4.7%.

$^1$H NMR (300 MHz, DMSO-d6) δ (ppm): 8.26-8.24 (d, 1H); 7.48-7.44 (m, 2H); 6.92-6.87 (m, 3H); 4.70-4.66 (d, 1H); 4.45-4.41 (d, 1H); 4.09-4.05 (t, 2H); 3.48-3.44 (t, 2H); 3.23 (s, 3H); 2.14 (s, 3H); 1.99-1.93 (q, 2H).

EXAMPLE 2

Preparation of Rabeprazole Form γ

100 g of rabeprazole sodium salt (amorphous) is dissolved at approximately 25° C. in 450 ml of ethyl acetate. The solution is kept at approximately 25° C. and 8 ml of sodium bicarbonate saturated solution is added. The mixture is kept under stirring at approximately 25° C. for 25 hours. The resulting white solid is filtered by suction, washed with 100 ml of ethyl acetate and dried under vacuum at 45° C. The resulting product has the same physical characteristics of the product obtained in example 1.

The invention claimed is:

1. Rabeprazole sodium, 2-[[[4-(3-methoxypropoxy)-3-methyl-2-pyridinyl]-methyl]sulfinyl]-1H-benzylimidazole sodium salt, in the monohydrate crystalline form having a water content approximately ranging from 4.5 to 5.0%.

2. Rabeprazole sodium according to claim 1, wherein the water content approximately ranges from 4.6 to 4.8%.

3. Rabeprazole sodium according to claim 1, having a DSC thermogram substantially as reported in FIG. 2.

4. Rabeprazole sodium according to claim 3, having an XRPD spectrum wherein the most intense diffraction peaks fall at 10.5; 18.0; 18.4; 19.4; 21.1; 21.7; 22.9; 23.3; 27.1; 31.6±0.2° in 2θ.

5. Rabeprazole sodium according to claim 4, having an XRPD spectrum substantially as reported in FIG. 1.

* * * * *